United States Patent [19]

Christensen et al.

[11] Patent Number: 4,904,483

[45] Date of Patent: Feb. 27, 1990

[54] METHOD FOR PRODUCTION OF AN UPGRADED COCONUT PRODUCT

[75] Inventors: Flemming M. Christensen, Basel, Switzerland; Hans A. S. Olsen, Holte, Denmark

[73] Assignee: Novo Industri A/S, Bagsvaerd, Denmark

[21] Appl. No.: 310,621

[22] Filed: Feb. 15, 1989

[30] Foreign Application Priority Data

Feb. 16, 1988 [DK] Denmark .............................. 0777/88

[51] Int. Cl.⁴ ................................................ A23L 1/36
[52] U.S. Cl. ....................................... 426/44; 426/52; 426/495
[58] Field of Search ........................ 426/49, 51, 52, 50, 426/44, 48, 61, 63, 495

[56] References Cited

U.S. PATENT DOCUMENTS 3,846,562 11/1974 Forkner ................................ 426/49
4,478,854 10/1984 Adler-Nissen et al. ................ 426/49
4,478,856 10/1984 Adler-Nissen et al. ................ 426/49

FOREIGN PATENT DOCUMENTS 2104259 8/1972 Fed. Rep. of Germany .
1402769 8/1975 United Kingdom .

*Primary Examiner*—Marianne Cintins
*Attorney, Agent, or Firm*—Birch, Stewart, Kolasch & Birch

[57] ABSTRACT

The method for production of an upgraded coconut product comprises the steps of: enzymatically treating an aqueous suspension of particles of coconut meat, which may be purified, with a cell wall degrading enzyme and a galactomannase, all essentially free from lipases, and separating a sludge phase. By means of this method a higher yield of directly recoverable clear coconut oil can be obtained in comparison to the yield of directly recoverably clear coconut oil produced by known methods for aqueous coconut oil extraction.

11 Claims, 4 Drawing Sheets

METHOD FOR PRODUCTION OF AN UPGRADED COCONUT PRODUCT

BACKGROUND OF THE INVENTION

The invention comprises a method for production of an upgraded coconut product, mainly coconut oil and coconut milk.

From GB patent No. 2 115 820, page 37 it appears that aqueous extraction of corn germ oil, olive oil, soy oil, rape seed oil and sunflower oil can be improved by means of an SPS-ase preparation which is essentially free from lipases.

If an attempt to produce coconut oil in the same manner, i.e. by aqueous extraction with an SPS-ase preparation, is carried out, very poor results in terms of directly recoverable clear coconut oil are obtained; the majority of the oil or the entire amount of the oil is present as an emulsion, from which it is difficult to recover the coconut oil. Thus, aqueous extraction of coconut oil seems to present special problems in comparison to other types of vegetable oil.

Thus, a need exists for a method for production of an upgraded coconut product including coconut oil by aqueous extraction, whereby a higher yield of directly recoverable clear coconut oil can be obtained in comparison to the yield of directly recoverable clear coconut oil produced by known methods for aqueous coconut oil extraction.

SUMMARY OF THE INVENTION

According to the invention it has been found that the above indicated need can be fulfilled, if a mixture of a cell wall degrading enzyme and a galactomannase, all essentially free from lipases, is used for the aqueous extraction.

Thus, the method according to the invention for production of an upgraded coconut product comprises the steps of enzymatically treating an aqueous suspension of particles of coconut meat, which may be purified, with a cell wall degrading enzyme and a galactomannase, all essentially free from lipases and separating a sludge phase.

As the enzyme treated aqueous suspension of particles of coconut meat can be separated into an aqueous phase, an oil phase, and a sludge phase, the upgraded coconut products produced according to the invention can be any of these three phases or a combination thereof, mainly coconut oil, coconut milk (the emulsified combined water and oil phase), and the sludge phase, which can be used as fodder. As appears later from this specification, in certain cases also a minor proportion of an emulsion phase can be present as a fourth separation phase.

In German published patent specification No. 21 04 259 a method for recovery of oil from cereal germs is described, whereby the cereal germs are dried in a specific manner, slurried in an aqueous medium and treated with cellulase. However, in contradistinction to the prior art method the method according to the invention is specifically directed to coconut meal as a starting material and to a specific combination of two well defined enzyme activities not disclosed in the German publication, and also, drying of the starting material is no critical aspect in relation to the method according to the invention.

In this specification with claims it is to be understood that the term "coconut meat, which may be purified", comprises all kinds of raw or purified coconut meat, e.g. copra or desiccated coconut.

In this specification with claims it is to be understood that the term "cell wall degrading enzyme" comprises a pectinase, an SPS-ase, a cellulase, and/or a protease. Thus, the term "a cell wall degrading enzyme" comprises one or more of the above enzymes, purified or in the form of crude preparations.

Examples of cell wall degrading enzymes appear from the following table.

| Enzyme | Preparation | Activity unit | Definition of activity unit |
|---|---|---|---|
| Pectinase | Pectinex 3xL | 3000 FDU/g | B-235d-GB |
| SPS-ase | SP-249 (PPS 1927) | 28 SPSU/g | B-297f-GB |
| Cellulase | CELLUCLAST ® 1.5L | 1500 NCU/g | B-153g-GB |
| Protease | ALCALASE ® 2.4l | 2.4 AU/g | B-318a-GB |

In this specification with claims, a galactomannase is a hemicellulase with a specific activity towards galactomannan. A galactomannase preparation is marketed by NOVO Industri A/S, Novo Alle,acu/e/, 2880 Bagsvaerd, Denmark under the trade mark Gamanase ®. Reference can be made to the pamphlet B-046d-GB, available on request from NOVO Industri A/S, like the above pamphlets indicated in the last column of the table. The definition of the activity unit for the galactomannase appears from the pamphlet B-046d-GB. The activity unit definitions in the above-mentioned pamphlets are hereby incorporated by reference.

The term "essentially free of lipase" means that the content of lipase in the enzyme preparation does not result in an increased release of free fatty acids from the oil during processing as compared to conventional processing.

It has been surprisingly found that the reaction mixture after the enzymatic treatment can be separated into a sludge phase, an aqueous phase, an emulsion phase and a large clear oil phase. If one or more cell wall degrading enzymes are used without the galactomannase, or if the galactomannase is used without cell wall degrading enzymes, no clear oil phase or an extremely small clear oil phase is formed.

In a preferred embodiment of the method according to the invention, 90% of the particles of the coconut meat is smaller than 1 mm. In this manner a higher yield of clear coconut oil is obtained.

In a preferred embodiment of the method according to the invention the aqueous suspension of particles of coconut meat is heat treated, preferably by jet cooking or UHT (ultra high temperature) treatment before the enzymatic treatment. In this manner the liberation of oil from the cells in the coconut meat is facilitated, and the effect of the later performed enzyme treatment is enhanced.

In a preferred embodiment of the method according to the invention the enzymatic treatment is carried out with a mixture of an SPS-ase preparation and a galactomannase. In this manner the largest possible yield of clear coconut oil is obtained. Another reason why this embodiment is advantageous is the fact that both the SPS-ase preparation indicated in the above table and the GAMANASE ® galactomannase preparation are practically free of lipases, and thus, lipase removal treatments are superfluous, and the quality of the coconut oil is not impaired during extraction.

In a preferred embodiment of the method according to the invention the galactomannase part of the enzyme treating agent comprises another hemicellulase besides the galactomannase. In this manner a larger yield of clear coconut oil is obtained.

In a preferred embodiment of the method according to the invention between 10 and 700 SPS-ase activity units and between $1.5 \times 10^6$ and $200 \times 10^6$ galactomannase activity units are used per kg of dry matter of coconut meat, and the enzymatic treatment is carried out between 1 and 6 hours. In this manner the optimum compromise between enzyme activities and treatment times can easily be selected in order to obtain maximum yield of clear coconut oil.

In a preferred embodiment of the method according to the invention the ratio between dry coconut meat and water in the aqueous suspension is between 0.10 and 0.25. In this manner the process is carried out with a relatively small water volume and yet efficiently.

In a preferred embodiment of the method according to the invention the separation of the coconut oil is carried out by centrifugation. In this manner the separation is carried out rapidly and efficiently.

In a preferred embodiment of the method according to the invention the separation of the coconut oil is carried out by decantation. In this manner the separation can be carried out by means of a cheap sedimentation apparatus, which typically can be used with advantage instead of a centrifuge.

BRIEF DESCRIPTION OF THE DRAWINGS

Also, reference is made to the accompanying FIGS. 1, 2, and 3, which will be explained in more detail later in this specification.

FIG. 1 and FIG. 2 are considered representative of an unsatisfactory technique in terms of the purpose of the invention. It appears that no clear oil phase is present at all in relation to FIG. 1, and that only a small clear oil phase is generated at a late stage in relation to FIG. 2.

FIG. 3 represents the method according to the invention. It appears that a large oil phase is developed after a relatively short treatment time. Thus, the method according to the invention is superior in comparison to the prior art methods.

DETAILED DESCRIPTION OF THE INVENTION

The invention is further illustrated in the following examples.

If the upgraded coconut product produced by means of the method according to the invention is coconut oil, the sludge and the aqueous phase are used as base materials for production of feed or food, and the emulsion is heated to around 90° C. in order to liberate the remaining small amount of oil.

Figure 1:
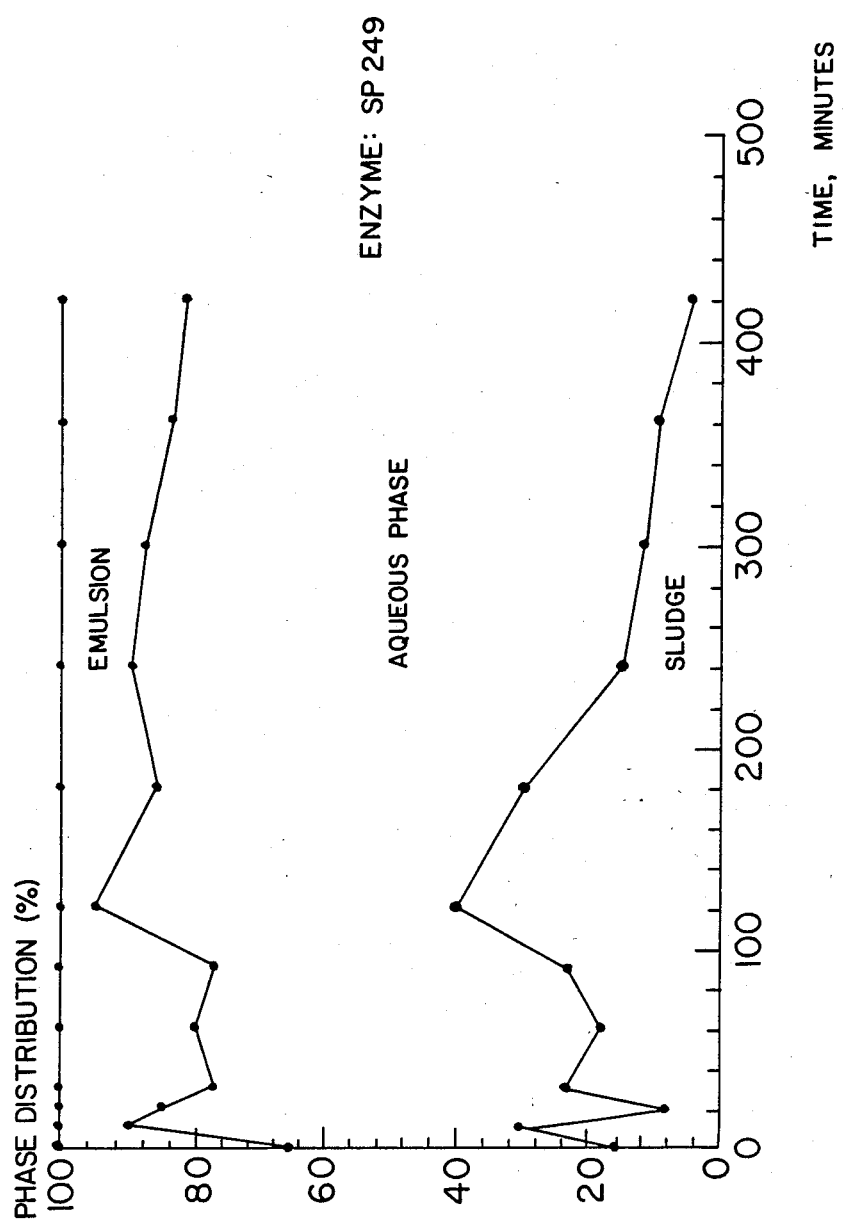
FIGS. 1 and 2 are graphs which show the relative amounts of the various phases after treatment of coconut meat with SPS-ase (FIG. 1) and GAMANASE® galactomannase (FIG. 2).
Figure 2:
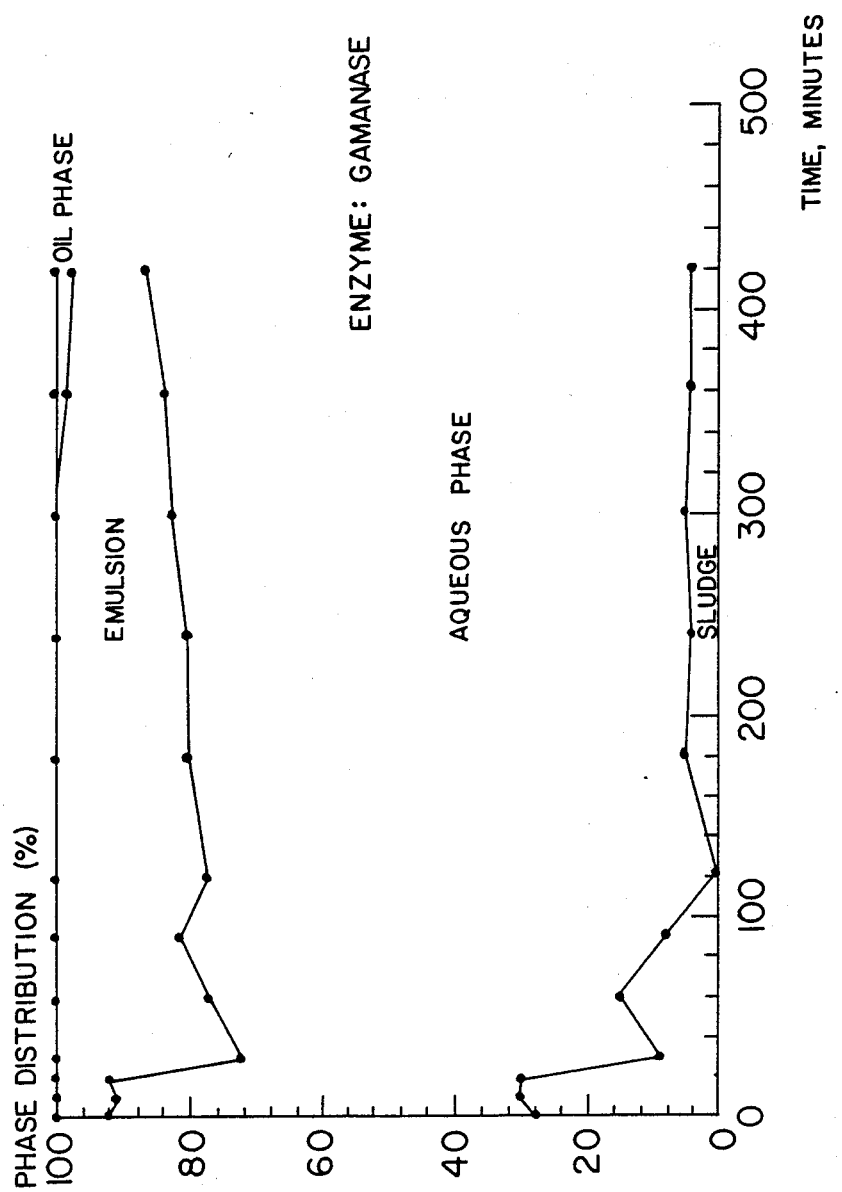
Figure 3:
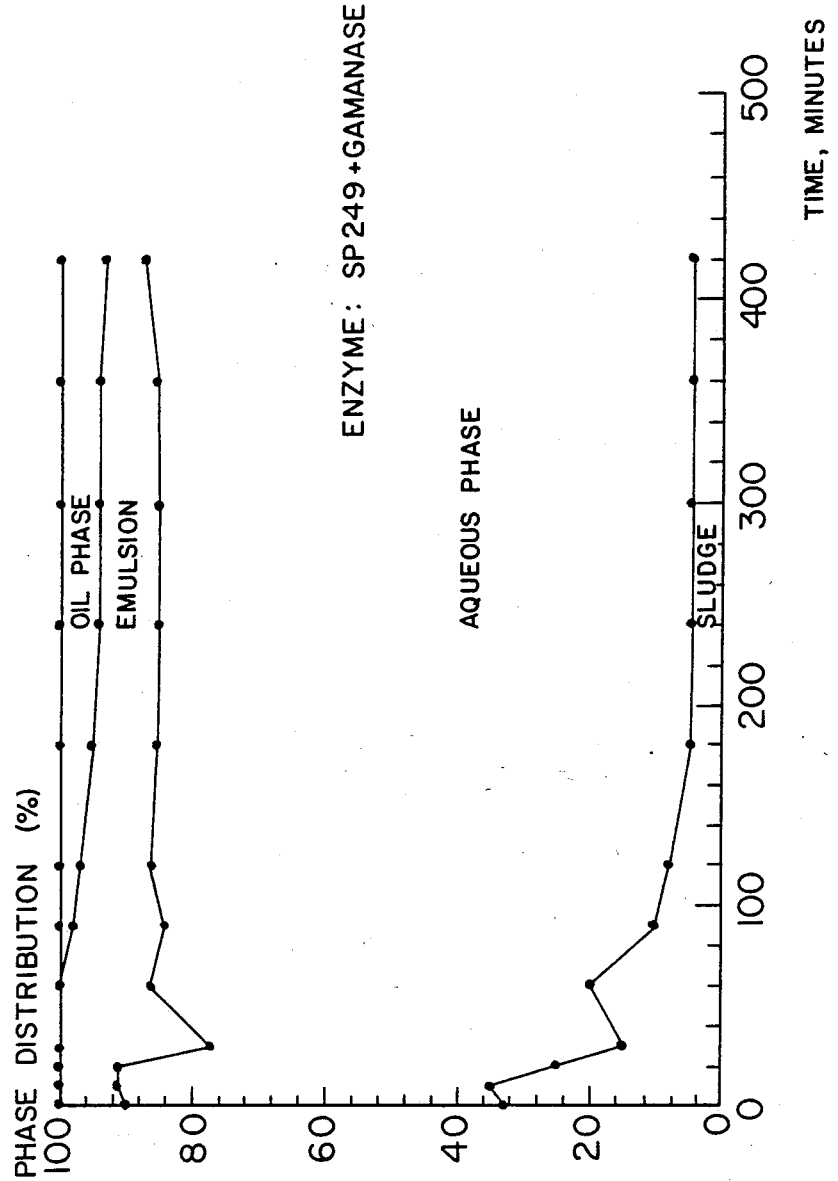
FIG. 3 is a graph which shows the relative amounts of the various phases after treatment of coconut meat with an enzyme mixture of SPS-ase preparation and GAMANASE® galactomannase. Thus.
Figure 4:
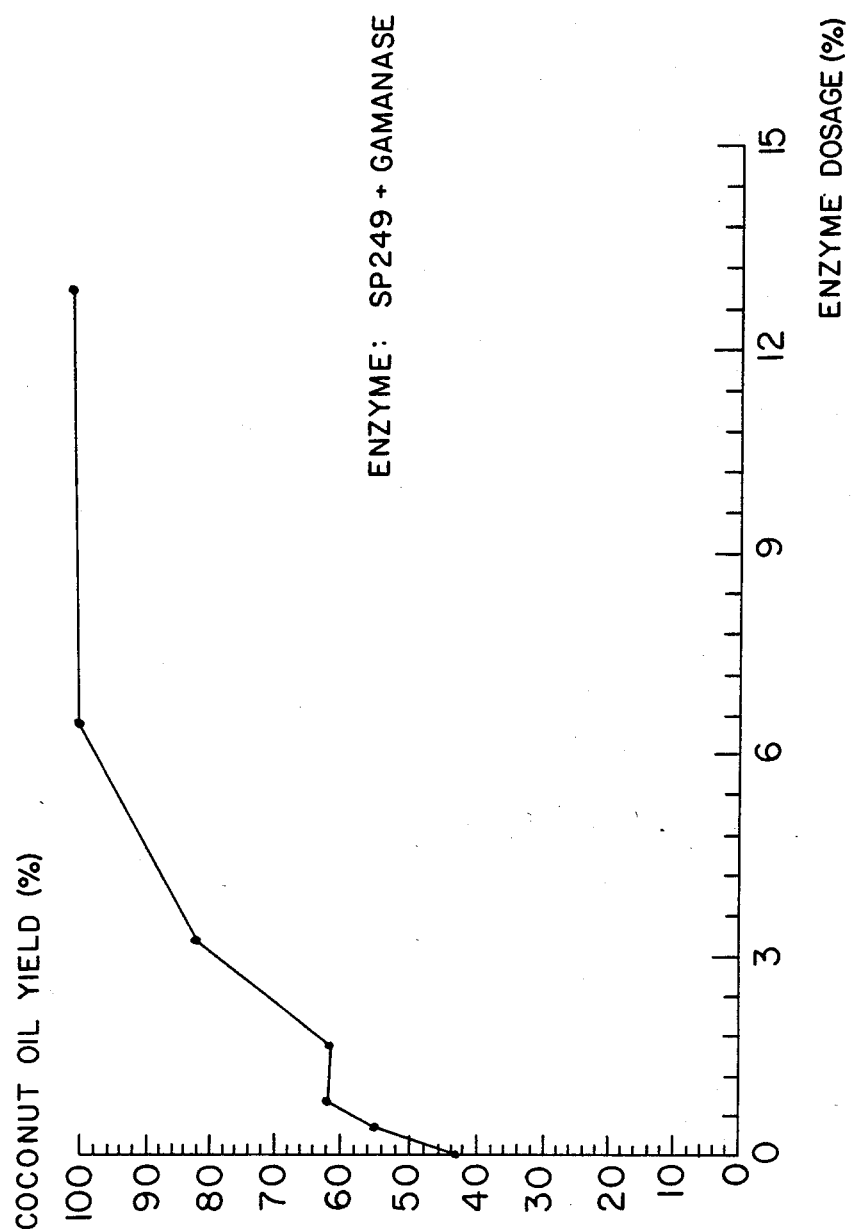
FIG. 4 is a dose-response curve which shows the effect of an increasing enzyme dosis on the coconut oil yield.

Example 1 is related to FIGS. 1, 2, and 3.
Example 2 is related to FIG. 4

Example 3 describes a pilot plant experiment according to the invention.

Example 4, 5, and 6 describe production of coconut milk.

EXAMPLE 1

125 g of desiccated coconut meat was mixed with 875 g of water in a reaction vessel. The slurry was homogenized for 2 minutes with an Ultra-Turrax laboratory homogenizer. The pH was adjusted to 4.5 by addition of 6N HCl with stirring.

The above procedure was carried out with 3 batches, A, B, and C. Enzymes were then added in the following manner:

Batch A: 5.94 g of SP-249 batch no. PPS 1927 was added, and enzyme hydrolysis took place for 420 minutes at 50° C. with continuous stirring.

Batch B: 26.4 g Gamanase was added and enzyme hydrolysis took place for 420 minutes at 50° C. with continuous stirring.

Batch C: 2.97 g of SP-249 batch no. PPS 1927 and 13.2 g Gamanase was added and enzyme hydrolysis took place for 420 minutes at 50° C. with continuous stirring.

For all 3 batches A, B, and C 10 ml samples were taken at times t=0, 10, 20, 30, 60, 90, 120, 180, 240, 300, 360 and 420 minutes. Each sample was boiled for 2 minutes to inactivate enzyme and was subsequently centrifuged in a laboratory centrifuge for 10 minutes at 4000 rpm. The phase distribution in volume-% (sludge, aqueous phase, emulsion and clear oil) was recorded and is shown in FIGS. 1–3. It can be seen that the combination of SP-249 and Gamanase gives rise to a large clear coconut oil fraction, whereas use of SP-249 or Gamanase alone gives no or only a small fraction of clear coconut oil.

EXAMPLE 2

43.8 g of desiccated coconut meat was mixed with 206.2 g of water in a reaction vessel. The slurry was homogenized for 1 minute with an Ultra-Turrax laboratory homogenizer. pH was adjusted to 4.5 by addition of 6N HCl with stirring.

The above procedure was carried out for 7 batches A–G. Enzymes were added in the following manner:

Batch A: No enzymes were added
Batch B: 0.0326 g of SP-249 PPS 1927+0.1439 g of Gamanase
Batch C: 0.0652 g of SP-249 PPS 1927+0.2877 g of Gamanase
Batch D: 0.1303 g of SP-249 PPS 1927+0.5768 g of Gamanase
Batch E: 0.2602 g of SP-249 PPS 1927+1.1550 g of Gamanase
Batch F: 0.5205 g of SP-249 PPS 1927+2.3060 g of Gamanase
Batch G: 1.0410 g of SP-249 PPS 1927+4.6170 g of Gamanase For all batches the hydrolysis was carried out at 50° C. for 4 hours.

After hydrolysis the slurry was boiled for 5 minutes in order to inactivate the enzymes, and subsequently the slurry was centrifuged for 10 minutes at 4200 rpm in a laboratory centrifuge. The supernatant was removed by decantation and analyzed for fat content whereby the oil yield could be calculated. The results are shown below and in FIG. 4.

| Trial | Total enzyme dose (SP-249 + Gamanase) (g per 100 g of dessicated coconut meat) | Oil yield (%) |
|---|---|---|
| A | 0 | 42.7 |
| B | 0.40 | 54.4 |
| C | 0.81 | 61.4 |
| D | 1.62 | 61.0 |
| E | 3.23 | 81.8 |
| F | 6.46 | 100.0 |
| G | 12.9 | 100.9 |

It is seen that the oil yield increases with increasing enzyme dose, and that an oil yield close to 100% can be obtained.

EXAMPLE 3

125 kg of desiccated coconut meat was mixed with 875 liters of water in a 1000 liter reaction vessel. The slurry was homogenized by means of an Ultra-Turrax Pilot Plant homogenizer. The pH was adjusted to 4.5 by addition of 6N HCl with stirring. 768 g of SP-249-PPS 1927 and 3412 g of Gamanase were added, and hydrolysis was carried out at 50° C. for 4 hours. The slurry was subsequently heated to 90° C. for 5 minutes in order to inactivate the enzymes.

Another homogenization was carried out with the Ultra-Turrax Pilot Plant homogenizer before the hot slurry was separated on an Alfa-Laval decanter centrifuge in order to remove solids.

The hot supernatant (90° C.) from the solid-liquid separation was separated on a liquid-liquid separating disc-centrifuge (Westfalia SB-7). The oil-containing phase was heated to 90° C. and separated once more on the liquid-liquid separating disc-centrifuge. Finally a third separation of the hot oil-containing phase (90° C.) was carried out to obtain 74 liters of completely clear coconut oil with 98.8% fat and 1.2% of water corresponding to a yield of 86%. The mass balance of the pilot plant trial is shown in the following table.

The oil composition was analyzed and compared to a coconut oil manufactured by conventional processing. The results are shown below:

|  | Enzymatically extracted coconut oil (%) | Standard coconut oil (%) |
|---|---|---|
| C-8 | 7.61 | 7 |
| C-10 | 6.36 | 7 |
| C-12 | 49.5 | 45 |
| C-14 | 18.9 | 20 |
| C-16 | 8.68 | 8 |
| C-16:1 | 0.15 | — |
| C-18 | 3.07 | 3 |
| C-18:1 | 4.90 | 7 |
| C-18:2 | 0.84 | 2 |
| FFA (free fatty acids) | 3.5 | — |

It is seen that the composition of the enzymatically extracted coconut oil is closely comparable to a standard quality coconut oil. An FFA-number of 3.5% is not high, when taking into consideration that the oil was manufactured in a batch process, and that the oil was not further purified or refined.

In the previous examples the upgraded coconut product produced by means of the method according to the invention was coconut oil. In the following examples the upgraded coconut product produced by means of the method according to the invention is coconut milk. Coconut milk is a stabilized emulsion of coconut oil in water and soluble components of the coconut meat.

EXAMPLE 4

This example illustrates a method for production of coconut milk on the basis of fresh coconut material on a lab scale.

The shells were removed, and the brown layer was peeled off. The pieces of coconut meat were washed in cold water, cut into smaller pieces and ground on a coffee mill. Then 281 g of ground coconut meat were mixed with 720 g of water and heated to 50° C. in a water bath with stirring. The pH-value was adjusted to 4.0 by means of 6N HCl.

| | | MASS BALANCE | | | | | | | | | |
|---|---|---|---|---|---|---|---|---|---|---|---|
| | | Phase distribution | | | | Dry matter | | Fat | | Protein | |
| | Mass/ amount | sludge (%) | liquid (%) | emuls. (%) | oil (%) | (%) | amount (kg) | (%) | amount (kg) | (%) | amount (kg) |
| Desiccated coconut | 125 kg | | | | | 97.02 | 121.28 | 57.4 | 71.75 | 6.10 | 7.6 |
| Water | 880 kg | | | | | | | | | | |
| Slurry | 1005 kg | 29 | 66 | 5 | 0 | | | | | | |
| After homogenizing | 1005 kg | 22 | 68 | 10 | 0 | | | | | | |
| HCl 33% | | | | | | | | | | | |
| SP-249 enzyme | 0.7688 kg | | | | | | | | | | |
| Gamanase enzyme | 3.4125 kg | | | | | | | | | | |
| Reaction mixture | 1040 kg | | | | | | | | | | |
| Decanter overflow | 0.94 ton | 2 | 86 | 12 | | 11.10 | 104.3 | 7.3 | 68.6 | 0.69 | 6.5 |
| Sludge from decanter | 38 kg | | | | | 34.08 | 13 | 2.2 | 0.76 | 3.15 | 1.2 |
| 1. Centrifugation | | | | | | | | | | | |
| Centrifugate | 520 kg | | | | | | | | | | |
| Emulsion | 270 l | | | | | | | | | | |
| Sludge | 38 kg | | | | | 17.87 | 6.8 | | | 1.272 | 0.48 |
| 2. Centrifugation | | | | | | | | | | | |
| Centrifugate | 180 l | 0.5 | 99.5 | 0 | 0 | | | | | | |
| Emulsion | 86 l | 0 | 16 | 10 | 74 | | | | | | |
| Sludge | 3 kg | | | | | | | | | | |
| 3. Centrifugation | | | | | | | | | | | |
| Centrifugate | | 0 | 100 | 0 | 0 | | | | | | |
| Clear oil | 74 l | 1 | 1.5 | 0.5 | 97 | | | 98.8 | 67 | | |
| Sludge | 10 kg | | | | | | | | | | |

This charge was divided into two equal parts. To part No. 1 was added 1.5 g of Gamanase and 1.5 g of SP-249; no enzyme was added to part No. 2.

The hydrolysis was carried out at 50° C. and with constant mechanical stirring. 100 ml samples were taken to the times 0, 1, 2, 4, and 6 hours. In order to inactivate the enzymes each sample was boiled for 5 minutes, and then it was centrifuged in a laboratory centrifuge for 20 minutes at 4200 rpm. The supernatant was decanted off, weighed and homogenized by means of an Ultra-Turrax laboratory homogenizer. A sample was taken for determination of dry matter. The residual material was lyophilized and subsequently analyzed for the content of fat and protein.

The below indicated table shows the yield of dry matter, fat and protein at the times indicated. It appears that after six hours of hydrolysis under the test conditions used in this experiment it is possible to increase the protein and oil yield from 39% and 68% respectively to 55% and 96% respectively.

| Sample time hours | enzyme +/− | Dry matter % | Protein % | Fat % |
| --- | --- | --- | --- | --- |
| 0 | + | 45.78 | 25.32 | 60.05 |
| 1 | + | 57.90 | 40.01 | 77.28 |
| 2 | + | 65.55 | 46.65 | 83.44 |
| 4 | + | 68.02 | 51.51 | 88.86 |
| 6 | + | 72.41 | 55.03 | 96.49 |
| 0 | − | 45.46 | 25.65 | 65.34 |
| 1 | − | 54.04 | 47.70 | 72.03 |
| 2 | − | 51.54 | 46.21 | 61.38 |
| 4 | − | 55.10 | 39.44 | 67.82 |
| 6 | − | 54.45 | 38.60 | 67.83 |

EXAMPLE 5

This example illustrates a method for production of coconut milk on the basis of dried coconut material on a lab scale Dried coconut meal was ground on a Bauermeister pin mill. Now the ground coconut meal was mixed with water to a coconut meal concentration of 15%, and the mixture was carried through a wet grinding mill (Fryma Zahnkolloidmühle, type MZ). Two 1000 ml hydrolysis samples were taken out (No. 1 and 2), and these were heated to 50° C. in a water bath with mechanical stirring, and the pH-value was adjusted to 4.0 by means of 6N HCl. To the 1000 ml of hydrolysis mixture No. 1 was added 1.5 g of GAMANASE and 1.5 g of SP 249. The hydrolysis was carried out at 50° C. and with constant stirring. 100 ml samples were taken out at times=0, 1, 2, 4, and 6 hours. Each sample was boiled for 5 minutes in order to inactivate the enzymes, and thereafter it was centrifuged in a laboratory centrifuge for 20 minutes at 4200 rpm. The supernatant was decanted, weighed and homogenized by means of an Ultra-Turrax homogenizer of the laboratory type. Then a sample was taken out for determination of dry matter. The residual mixture was lyophilized, and then the fat and protein content was determined. Hydrolysis sample No. 2 (1000 ml) was treated as No. 1, except that no enzyme was added.

The below indicated table shows the yield of dry matter, fat and protein at the times indicated. It appears that after 6 hours of hydrolysis under the test conditions indicated in this experiment it is possible to increase the protein and oil yield from 16 and 76% respectively to 64 and 95% respectively.

| Sample time hours | enzyme +/− | Dry matter % | Protein % | Fat % |
| --- | --- | --- | --- | --- |
| 0 | + | 53.82 | 16.93 | 71.14 |
| 1 | + | 63.68 | 58.23 | 82.64 |
| 2 | + | 74.12 | 61.35 | 89.79 |
| 4 | + | 78.13 | 61.61 | 92.37 |
| 6 | + | 81.99 | 63.67 | 94.63 |
| 0 | − | 52.00 | 16.14 | 68.73 |
| 1 | − | 54.09 | 18.95 | 71.12 |
| 2 | − | 53.43 | 19.82 | 74.25 |
| 4 | − | 57.46 | 19.57 | 74.77 |
| 6 | − | 57.57 | 15.64 | 75.77 |

EXAMPLE 6

This example illustrates a method for production of coconut milk on the basis of dry coconut material on a pilot plant scale.

78.5 kg of dried coconut meal was ground on a Bauermeister pin mill. Now the coconut meal was mixed with 429.5 kg of water in a 600 l reaction tank and pumped into the hopper of a wet grinding mill (Fryma, Zahnkolloidmühle, type MZ). The ground mixture was pumped back into the tank and heated to 50° C. The pH-value was adjusted to 4.0 by means of 37% HCl with stirring. 762 g of GAMANASE and 762 g of SP 249 was added, and the hydrolysis was carried out for 4 hours at 50° C. with constant stirring. Then the mixture was heated to 90° C. for five minutes in order to inactivate the enzymes. The sludge was removed from the 50° C hot mixture by means of an Alfa-Laval decanter, and the thus produced coconut milk was concentrated by evaporation on a Niro Atomizer evaporator to a dry matter content of 65.7% and a protein and fat content of 4.37% and 51.8%, respectively.

The below indicated table shows the yield of dry matter, fat and protein at the times indicated. It appears that after four hours of hydrolysis under the test conditions used in this experiment it is possible to obtain an oil yield of 95% and a protein yield of 80%.

| Sample time hours | enzyme +/− | Dry matter % | Protein % | Fat % |
| --- | --- | --- | --- | --- |
| 0 | + | 42.11 | 38.97 | 72.45 |
| 1 | + | 62.62 | 57.07 | 84.97 |
| 2 | + | 49.77 | 72.02 | 91.27 |
| 3 | + | 57.30 | 78.59 | 94.73 |
| 4 | + | 74.08 | 79.55 | 95.18 |

We claim:

1. A method for production of an upgraded coconut product, which comprises the steps of:
   enzymatically treating an aqueous suspension of particles of coconut meat with a cell wall degrading enzyme and a galactomannase, all essentially free from lipases, wherein said cell wall degrading enzyme and said galactomannase are present in an amount effective for generation of a clear oil phase containing the majority of the oil after the enzymatic treatment is completed; and
   separating a sludge phase.

2. The method according to claim 1, wherein 90% of the particles of the coconut meat are smaller than 1 mm.

3. The method according to claim 1, wherein the aqueous suspension of particles of coconut meat is heat treated before the enzymatic treatment.

4. The method according to claim 1, wherein the enzymatic treatment is carried out with a mixture of an SPS-ase preparation and a galactomannase wherein said SPS-ase is said cell wall degrading enzyme.

5. The method according to claim 1, wherein the galactomannase part of the enzyme treating agent comprises another hemicellulase besides the galactomannase.

6. The method according to claim 4, wherein between 10 and 700 SPS-ase activity units and between $1.5 \times 10^6$ and $200 \times 10^6$ galactomannase activity units are used per kg dry matter of coconut meat, and the enzymatic treatment is carried out between 1 and 6 hours.

7. The method according to claim 1, wherein the ratio between dry coconut meat and water in the aqueous suspension is between 0.10 and 0.25.

8. The method according to claim 1, wherein the separation of sludge phase is carried out by centrifugation.

9. The method according to claim 1, wherein the separation of the coconut oil is carried out by decantation.

10. The method according to claim 1, wherein the particles of coconut meat are purified prior to enzymatic treatment.

11. The method according to claim 1, wherein between 10 and 700 SPS-ase activity units and between $1.5 \times 10^6$ and $200 \times 10^6$ galactomannase activity units are used per kg dry matter of coconut meat.

* * * * *